US00PP31284P2

(12) United States Plant Patent
Hansen

(10) Patent No.: US PP31,284 P2
(45) Date of Patent: Dec. 24, 2019

(54) ***PULMONARIA* PLANT NAMED 'PRETTY IN PINK'**

(50) Latin Name: ***Pulmonaria* hybrid**
Varietal Denomination: Pretty in Pink

(71) Applicant: Hans A Hansen, Zeeland, MI (US)

(72) Inventor: Hans A Hansen, Zeeland, MI (US)

( * ) Notice: Subject to any disclaimer, the term of this patent is extended or adjusted under 35 U.S.C. 154(b) by 0 days.

(21) Appl. No.: 16/350,939

(22) Filed: Feb. 1, 2019

(51) Int. Cl.
*A01H 5/02* (2018.01)

(52) U.S. Cl.
USPC ..... Plt./473

(58) Field of Classification Search
USPC ..... Plt./473
CPC ..... A01H 5/02
See application file for complete search history.

*Primary Examiner* — Annette H Para

(57) ABSTRACT

A new and distinct hybrid of Lungwort plant named *Pulmonaria* 'Pretty in Pink' characterized by silver spotting on medium green foliage, medium pink flower buds on dense, upright, highly branched stems, that open and retain their bright rose-pink color on mostly outright to slightly drooping campanulate flowers. The new plants show excellent vigor and good mildew resistance.

1 Drawing Sheet

Botanical denomination: *Pulmonaria* hybrid.
Variety designation: 'Pretty in Pink'.

STATEMENT REGARDING PRIOR DISCLOSURES UNDER 37 CFR 1.77(b)(6)

The first public disclosure of the claimed plant, in the form of a photograph and brief description on a website operated by Walters Gardens, Inc. on Feb. 1, 2018. The claimed plant was first sold on Jul. 9, 2018 by Walters Gardens, Inc., who obtained the plant and all information relating thereto, from the inventor. No plants of *Pulmonaria* 'Pretty in Pink' have been sold in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The present invention relates to a new and distinct cultivar of *Pulmonaria* and given the cultivar name of 'Pretty in Pink'. *Pulmonaria* is in the family Boraginaceae. The new cultivar originated from a multiple generation crossing beginning with 'Pink Haze' U.S. Plant Pat. No. 14,307 selected in a private garden in Zeeland, Mich., USA in May of 2015.

The new plant was initially asexually propagated at the same nursery in the summer of 2016 by division of the rhizome and followed by plant tissue culture of the shoot tip. The result plants have shown themselves to be stable and true to type in successive generations of asexual propagation by division at the same nursery in Zeeland, Mich. and also through shoot tip tissue culture.

SUMMARY OF THE INVENTION

Compared with 'Pink Haze', the new plant has darker pink flower buds, the foliage is more ovate and less oblanceolate and the color is more yellow-green with dapped spots of lighter yellow-green. Compared with the male parent and female parents, the new cultivar has better pink flower color and the flower stems are more upright. The nearest comparison plants known to the inventor include: 'Dora Bielefeld' (not patented), and 'Pierre's Pure Pink' (not patented). 'Pierre's Pure Pink' has lighter pink flowers that are more cupped and not as flared, and the habit and foliage are smaller. 'Dora Bielefeld' has smaller and more cupped flowers and the foliage is pale green.

*Pulmonaria* 'Pretty in Pink' is distinct from all other lungwort plants known to the inventor by the following combined traits:

1. Medium pink flower buds on upright highly-branched stems in mid-spring;
2. Pink flower buds open to consistently bright, rose-pink, campanulate flowers on numerous dense panicles;
3. Medium green foliage with prominent silver spotting on both cauline leaves and basal leaves arising after flowering;
4. Excellent vigor producing compact mounded habit; and
5. Foliage shows good mildew resistance.

BRIEF DESCRIPTION OF THE DRAWING

The photographs of the new plant demonstrate the unique traits of the new plant and the overall appearance. The colors are as accurate as reasonably possible with color reproductions. Variation in ambient light spectrum, source and direction may cause the appearance of minor variation in color. The accompanying photographs are of a three-year-old plant growing in a partially shaded garden in Zeeland, Mich.

DETAILED PLANT DESCRIPTION

Figure 1:
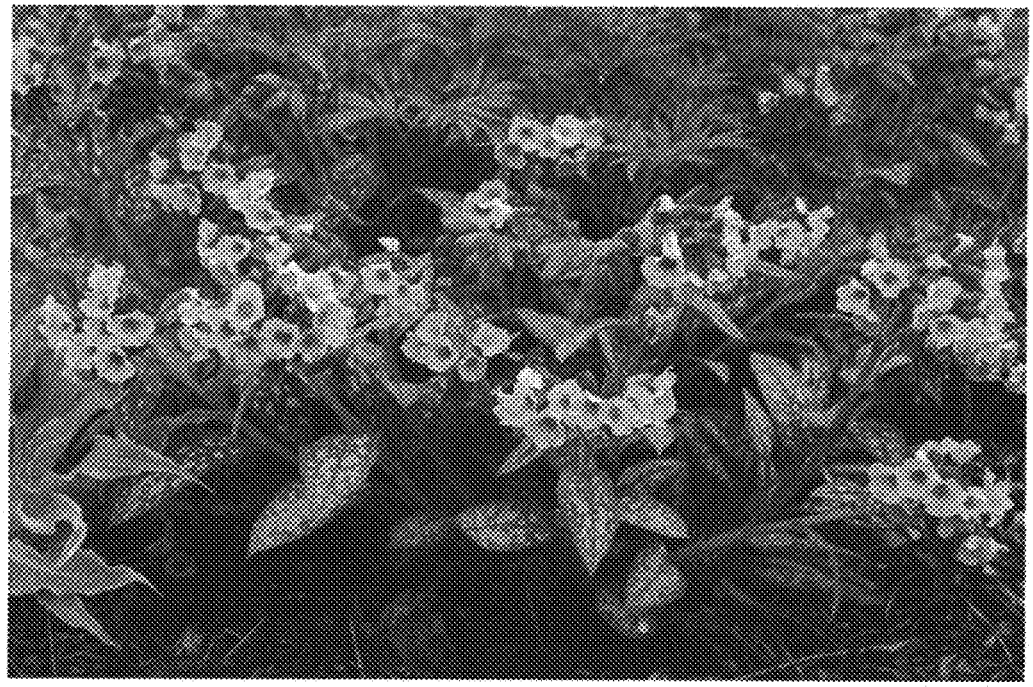
FIG. 1 shows the spring foliage and flowering habit of the new plant.
Figure 2:
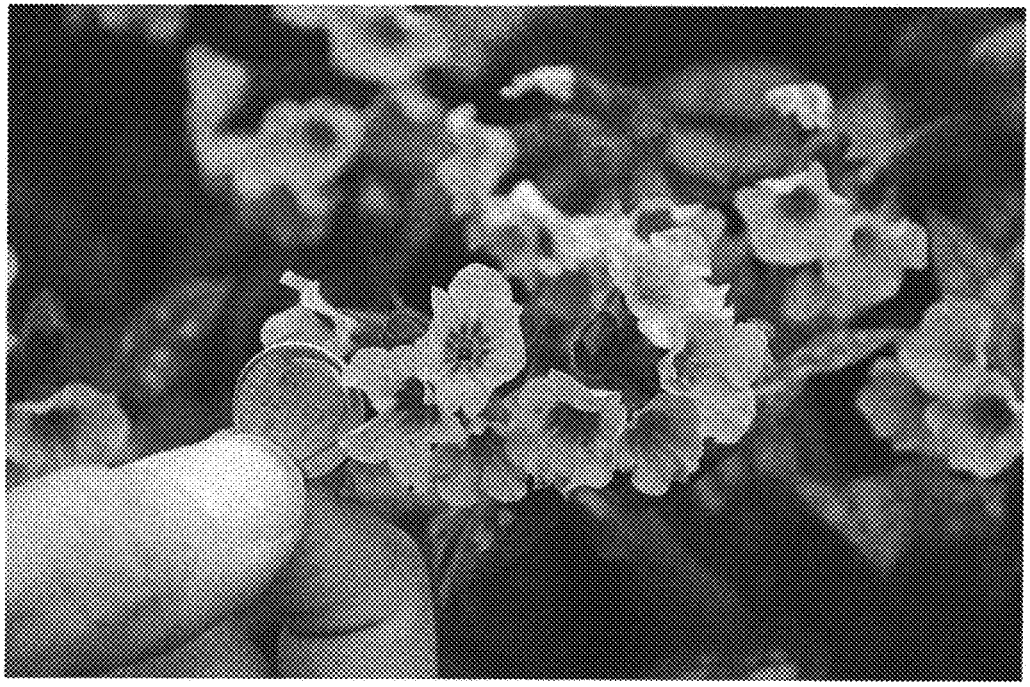
FIG. 2 shows a close-up of flowers and buds of the new plant.

The following is a detailed description of a three-year-old plant of 'Pretty in Pink' as grown outdoors in a partially shaded trial plot at a wholesale nursery in Zeeland, Mich. Plants of the new cultivar have not been tested under all possible conditions. The phenotype may vary with changes in environment, climate, and cultural conditions without change however in the genotype. The color references are in accordance with the 2015 edition of The Royal Horticultural Society Colour Chart except where general color dictionary terms are used.

Parentage: Multigenerational crossing originating with 'Pink Haze';

Plant habit: Herbaceous, perennial forming low, multi-stemmed, flowering mound in spring followed in summer producing a clumping basal rosette;

Size: With spring flowering 76.0 cm wide and 37.0 cm tall; summer foliage size 80.0 cm wide and 35.0 cm tall;

Vigor: Excellent; produces rooted plantlet in tissue culture in about 14 to 20 days; fills a 3.8 liter container in about 10 weeks from tissue cultured plug;

Propagation: Division of the crown or tissue culture;

Roots: Fleshy, to about 3.0 mm thick; near white depending on soil type;

Leaves: In basal rosette; developing prior to cymes dehiscing; simple; oblanceolate; hispid to hispidulous abaxial and adaxial; apex acute; base attenuate, semi-clasping; margin entire, ciliolate; with spots on adaxial surface between 0.5 mm and frequently running together to about 0.0 mm in diameter;

Leaf size: To about 24.0 cm long and 8.0 cm wide at the center; average about 22.0 cm long and 7.2 cm wide;

Cauline leaf: Alternate; simple; ovate to oblanceolate; hispidulous abaxial and adaxial; acute apex; base attenuate, sessile, clasping; margin ciliolate and entire; with spots on adaxial surface between 0.5 mm and 4.0 mm diameter; to 8.5 cm long and 25.0 mm wide decreasing distally; average about eight cauline leaves per stem below flowers; cauline leaves and stems not persistent, drying after seed production;

Leaf color (basal and cauline): Adaxial between RHS 137A and RHS 137B with irregular spotted silver portions nearest RHS 194C; abaxial between RHS 147B and RHS 147C;

Venation: Pinnate; only abaxial and adaxial midrib distinct; hispid to hispidulous abaxial and adaxial;

Vein color: Adaxial midrib nearest RHS 146D; abaxial midrib nearest RHS 146D;

Petiole description: Concavo-convex; scabrous;

Petiole size: To about 11.0 cm long and 12.0 mm wide at base; average about 10.0 cm long and 11.0 mm wide;

Petiole color: Adaxial and abaxial margin nearest RHS 137B; adaxial center nearest 145C; abaxial longitudinal center nearest RHS 145C in basal portion, distally nearest a blend between RHS 160C and RHS 146D;

Inflorescence: Terminal branched cyme; about 80 cymes per plant with 15 to 27 flowers per cyme, average 21 flowers per cyme;

Flowering period: Beginning about mid-April and continuing for about four weeks;

Flower longevity: Individual flowers open for about four days;

Flower fragrance: None detected;

Peduncle: Cylindrical; hispidulous; about 37 cm long, about 5.0 mm diameter at base; upright;

Peduncle color: Blend between RHS 146D and RHS N144D;

Pedicel: Cylindrical; hispidulous; to about 2.0 mm long and about 1.0 mm diameter; color nearest RHS 146D;

Flower bud: Oblong ovoid; to about 14.0 mm long and 5.0 mm wide at petals and calyx about 3.5 mm diameter;

Flower bud color: One day prior to opening calyx nearest RHS 138B with exposed petal nearest RHS 51B;

Flower: Campanulate, actinomorphic, forming funnelform corolla; size 20.0 mm long and 18.0 mm wide;

Petals: Typically five; fused in basal 15.0 mm with rounded apices; margins entire; glabrous abaxial and adaxial except for adaxial pubescent with tufts of hairs about 2.0 mm long about 8.0 mm to 11.0 mm from base; about 19.0 mm long and 9.0 mm across at fusion;

Petal color: Young adaxial face nearest RHS 64D, tube nearest RHS 155C, abaxial face nearest RHS 63C, tube base nearest RHS 155C with spots near mouth of tube nearest RHS 64A; mature adaxial face nearest RHS 63C, base nearest RHS NN155C with spots of nearest RHS 77A, abaxial face nearest RHS 55C, tube base nearest RHS 155C with two spots per petal between tube and face of nearest RHS 70A;

Calyx description: Campanulate; abaxial and adaxial hirsutulous; about 11.0 mm long and 4.0 mm across at apex;

Sepals: Five; apices narrowly acute; about 11.0 mm long and 2.5 mm across at fusion, fused in basal about 8.0 mm; hispid abaxial and hispidulous adaxial;

Sepal color: Adaxial nearest RHS 146C; abaxial nearest RHS 138B with tinting of nearest N186C in apical 2.0 mm, Gynoecium: One; pistil to about 13 mm long;

Ovary: Partially inferior, four-chambered; globose to about 1.5 mm diameter; color nearest RHS 144C;

Style: Cylindrical; glabrous; about 8.0 mm long and about 0.5 mm diameter at base; color nearest RHS 157B;

Stigma: Flattened; bifid; to about 0.5 mm diameter and 0.3 mm tall; color nearest RHS 155A;

Androecium: Five;

Filament: Entirely adnate about 3.5 mm above base of inner corolla; color nearest RHS NN155D;

Anther: Fused to petal; introrse; dorsifixed; longitudinal; oblong about 2.5 mm long and 1.0 mm diameter; color nearest RHS N187A;

Pollen: Abundant; color RHS NN155B;

Seed: To about four per flower, held within calyx; globose with rounded base and acute apex; about 1.0 mm diameter; color nearest RHS N199B;

Resistance to pest and diseases: *Pulmonaria* 'Pretty in Pink' has good mildew resistance, but not shown any resistance or susceptibility beyond that common to other lungwort.

Hardiness: The new plant is hardy from at least USDA hardiness zones 3 through 9.

I claim:

1. The new and distinct cultivar of *Pulmonaria* plant named 'Pretty in Pink' as herein described and illustrated.

* * * * *